(12) United States Patent
Rich et al.

(10) Patent No.: US 6,968,743 B2
(45) Date of Patent: Nov. 29, 2005

(54) IMPLANTABLE SENSING DEVICE FOR PHYSIOLOGIC PARAMETER MEASUREMENT

(75) Inventors: Collin A. Rich, Ypsilanti, MI (US);
Yafan Zhang, Plymouth, MI (US);
Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 273 days.

(21) Appl. No.: 10/054,331

(22) Filed: Jan. 22, 2002

(65) Prior Publication Data

US 2002/0115920 A1 Aug. 22, 2002

Related U.S. Application Data

(60) Provisional application No. 60/263,327, filed on Jan. 22, 2001, and provisional application No. 60/278,634, filed on Mar. 26, 2001.

(51) Int. Cl.[7] .................................................. G01L 9/12
(52) U.S. Cl. ..................................................... 73/724
(58) Field of Search .................. 73/708, 714, 715–727, 73/756; 338/3, 4; 361/283.1–283.4; 600/22, 25

(56) References Cited

U.S. PATENT DOCUMENTS

| | | | | |
|---|---|---|---|---|
| 4,023,562 A | | 5/1977 | Hynecek et al. ........ 128/2.05 E |
| 4,846,191 A | | 7/1989 | Brockway et al. .......... 128/748 |
| 5,081,437 A | * | 1/1992 | Mosser et al. ................. 338/2 |
| 5,259,248 A | * | 11/1993 | Ugai et al. ..................... 73/721 |
| 5,531,787 A | * | 7/1996 | Lesinski et al. ............... 623/10 |
| 5,535,752 A | | 7/1996 | Halperin et al. ............ 128/670 |
| 5,706,565 A | | 1/1998 | Sparks et al. ............... 29/25.42 |
| 5,909,280 A | * | 6/1999 | Zavracky ..................... 356/454 |
| 5,984,859 A | * | 11/1999 | Lesinski ....................... 600/25 |
| 6,068,589 A | * | 5/2000 | Neukermans ................ 600/25 |
| 6,201,980 B1 | | 3/2001 | Darrow et al. |
| 6,268,161 B1 | | 7/2001 | Han et al. |
| 6,328,699 B1 | | 12/2001 | Eigler et al. |

FOREIGN PATENT DOCUMENTS

| | | |
|---|---|---|
| WO | WO 00/13003 | 3/2000 |
| WO | WO 00/19888 | 4/2000 |
| WO | WO 00/30534 | 6/2000 |

OTHER PUBLICATIONS

A Passive Wireless Integrated Humidity Sensor, Timothy Harpster et al. 2001, pp. 553–557, no month.
Electrodeposited Copper Inductors for Intraocular pressure Telemetry; R. Puers et al.; 2001 pp. 124–129, no month.
Hermetically Sealed Inductor–Capacitor (LC) Resonator for Remote Pressure Monitoring; Eun–Chul Park et al.; Sep. 8, 1998; pp. 7124–7128.
Integrated MEMS for Pressure Transponder, Kim et al. 1997 pp. 1011–1014, no month.

* cited by examiner

*Primary Examiner*—William Oen
(74) *Attorney, Agent, or Firm*—Gary M. Hartman; Domenica N.S. Hartman; Hartman & Hartman (57) ABSTRACT

The present invention defines an implantable microfabricated sensor device for measuring a physiologic parameter of interest within a patient. The sensor device includes a substrate and a sensor, integrally formed with the substrate, that is responsive to the physiologic parameter of interest. At least one conductive path is integrally formed with said substrate and coupled to the sensor. Connected to the conductive path is an active circuit. The active circuit is further electrically connected to the sensor.

35 Claims, 6 Drawing Sheets

IMPLANTABLE SENSING DEVICE FOR PHYSIOLOGIC PARAMETER MEASUREMENT

CROSS REFERENCE TO RELATED APPLICATION

This application claims priority to prior U.S. provisional application No. 60/263,327 (filed Jan. 22, 2001) and U.S. provisional application No. 60/278,634 (filed Mar. 26, 2001).

BACKGROUND OF THE INVENTION

Field of the Invention

The present invention generally relates to the field of micro-electromechanical systems (MEMS) sensors and more specifically to a MEMS capacitive sensor specifically adapted and optimized for implantation into the body of a patient to enable measurement one or more physiologic parameters.

A number of different biologic parameters are strong candidates for monitoring with invasive medical tools. These parameters include, but are not limited to blood pressure, blood flow, intracranial pressure, intraocular pressure, glucose levels, blood chemistry, blood temperature, etc. Microfabricated sensors, in particular, are good candidates for minimally invasive tools since they can provide high fidelity signals in a small package.

Efforts to use microfabricated sensors for invasive medical applications have typically been limited, however, because of various integration issues. Several factors contribute to this limitation, including: 1) difficulty in mechanically integrating a microfabricated pressure sensor into the soft materials and/or narrow geometries of medical devices such as catheters and guidewires; 2) difficulty in integrating multiple leads into the shaft of a medical device; and 3) the requirement, in the case of differential pressure sensors (or derivative devices), to have a lumen for communication with an atmospheric reference pressure.

These integration issues have resulted in prior art devices that require a complex electromechanical assembly with many dissimilar materials, which will result in significant temperature- and aging-induced drift over time. Such assemblies may also be too large for many desirable applications, including intraocular pressure monitoring and/or pediatric applications. Finally, complex assembly processes will make such devices prohibitively expensive to manufacture for widespread use.

As an alternative to conventionally fabricated devices, microfabricated sensors have also been proposed. One such device is taught by Darrow (U.S. Pat. No. 6,201,980). Others are reported in the literature (see, e.g. Park, et al., Jpn. J. Appl. Phys., 37 (1998), pp. 7124–7128; Puers, et al., J. Micromech. Microeng. 10 (2000), pp. 124–129; Harpster et al., Proc. 14$^{th}$ IEEE Int'l. Conf. Microelectromech. Sys. (2001), pp. 553–557).

In view of the above and other limitations on the prior art, it is apparent that there exists a need for an improved MEMS sensor, one capable of overcoming the limitations of the prior art regarding implantation while being optimized for signal fidelity and microfabrication. It is therefore an object of the present invention is to provide a minimally invasive medical device for on-site physiologic parameter measurement.

Also an object of this invention is to provide microfabricated sensing device adapted for implantation within the body of patient in which active circuitry is integrated into the sensing device.

Also an object of this invention is to a microfabricated sensing device adapted for implantation within the body of patient in which active circuitry is integrated into the sensing device.

A further object of the invention is to provide a microfabricated implantable sensing device exhibiting high stability and low drift.

BRIEF SUMMARY OF THE INVENTION

In overcoming the limitations of the prior art and achieving the above objects, the present invention provides for a sensing device for implantation into the body of a patient and which permits conditioning and analysis of the signal from a sensor portion of the device on the device itself.

In achieving the above, the present invention provides a sensing device in which the sensing and signal conditioning components are located on a monolithic structure that can be entirely implanted in the human body. The monolithic structure includes a substrate on which a sensor is integrally microfabricated and configured to be responsive to a physiologic parameter of a patient's body. For example, the sensor may be a capacitive sensor adapted to measure pressure, e.g., blood pressure.

In addition to the sensor, the monolithic structure of the implantable sensing device includes active circuitry that conditions the signal from the sensor for immediate signal processing, for example, data logging, error correction, encoding, analysis and/or multiplexing of multiple sensor inputs. As such, the active circuitry may be integrally microfabricated in the substrate during microfabrication of the sensor and employing the same fabrication techniques. Alternatively, the active circuitry may be added to the substrate of the device after initial microfabrication of the sensor and thereafter connected to the sensor through wirebonds or leads integrally fabricated with the sensor.

Locating this circuitry on the monolithic structure in close proximity to the microfabricated sensor minimizes parasitic effects and other factors that could lead to degradation in the received signal and error in the measured physiologic parameter. Further objects and advantages of the present invention will become apparent to those skilled in the art from a review of the drawings in connection with the following description and dependent claims.

DETAILED DESCRIPTION OF THE PREFERRED EMBODIMENTS

Figure 1:
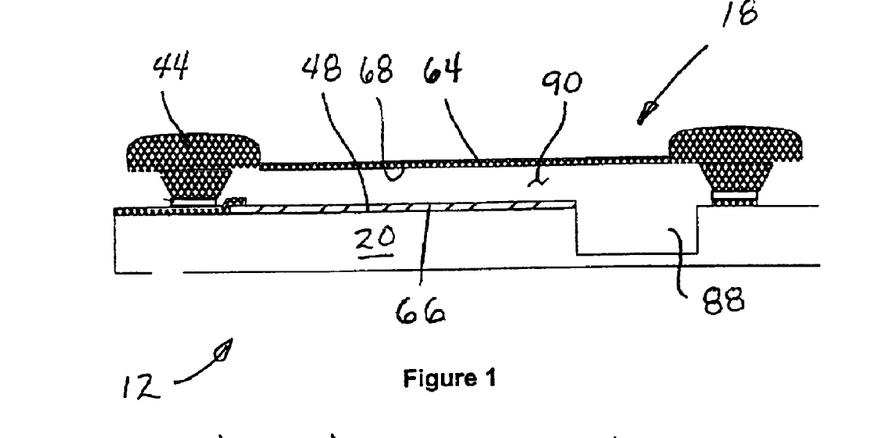
FIG. 1 is a cross-sectional representation of a microfabricated pressure sensor according to the principles of the present invention.

In order to provide a practical minimally invasive medical device for on-site physiologic parameter measurement, the present invention provides for a microfabricated sensing device 12 having an integrated capacitive pressure sensor 18. Referring to FIG. 1, a cross section of a preferred embodiment of the capacitive sensor 18 is illustrated therein.

The capacitive pressure sensor 18 includes a main substrate 20 (preferably 7740 Pyrex glass) over which an upper cap layer 44 is formed. Preferably, the upper cap layer 44 is of monocrystalline silicon and highly doped to be conductive.

The upper cap layer 44 is formed to define a diaphragm 64. The diaphragm 64 constitutes and may also be referred to as the moveable electrode of the pressure sensor 18. A fixed electrode 66 of the pressure sensor 18 is defined by a conductive layer formed on the upper face 48 of the substrate 20, in a position immediately below the moveable electrode or diaphragm 64. If desired, an additional conductive layer may be located on the underside 68 of the moveable electrode 64. To prevent shorting between the moveable electrode 64 (as defined by either the diaphragm itself or the diaphragm and the conductive layer) and the fixed electrode 66, one or both of the electrodes 64 and 66 may be provided with a thin dielectric layer (preferably less than 1000 Å) deposited thereon.

The upper cap layer 44 is bonded to the substrate 20 preferably via a hermetic sealing process. Alternatively, a post-bond coating of the entire sensor 18 may be used to establish hermeticity. In either situation, steps are taken to minimize the residual gas pressure within the sensor 18 after a hermetic seal is established. Once the initial hermetic seal is achieved, gas may be trapped in the interior of the sensor 18 due to continued outgassing of the interior surfaces and/or the bonded regions. The pressure of the residual gas will increase within the interior chamber 90 of the pressure sensor 18 as the diaphragm 64 deflects during normal operation. This residual gas may affect the overall sensitivity of the pressure sensor 18 by effectively increasing the spring constant of the diaphragm 64. Additionally, the residual gas will expand and/or contract with changes in the temperature of the sensor 18 itself, causing signal drift.

To compensate for the various negative effects of any residual gas, the pressure sensor 18 is provided with a displacement cavity 88. This displacement cavity 88 is generally seen in FIG. 1 and is in communication, either directly or through a small connecting channel, with the interior chamber 90 of the pressure sensor 18, defined between the moveable electrode 64 and the fixed electrode 66. The displacement cavity 88 is sized such that the total internal sensor volume, the combined volume of the displacement cavity 88 and the interior chamber 90, varies minimally with deflection of the diaphragm 64 over its operational range of displacement. By minimizing the overall change in volume with deflection of the diaphragm 64, the effect of the residual gasses are minimized and substantially eliminated. In the preferred embodiment, the volume of the displacement cavity 88 is approximately ten times greater than the volume of the chamber 90. To further reduce temperature induced drift and to increase the sensitivity of the sensor 18, lower pressures within the internal volume 90 should be used.

Under normal operation, pressure applied to the exterior or top surface of the capacitive pressure sensor 18 causes the diaphragm 64 (or at least the center portions thereof) to deflect downward toward the fixed electrode 66. Because of the change in distance between the fixed electrode 66 and the moveable electrode 64, a corresponding change will occur in the capacitance between the two electrodes. The applied pressure is therefore translated into a capacitance. With this in mind, it is seen that the capacitance pressure sensor 18 may be operated in either of two modes—a "proximity" mode and a "touch" mode.

Figure 2:
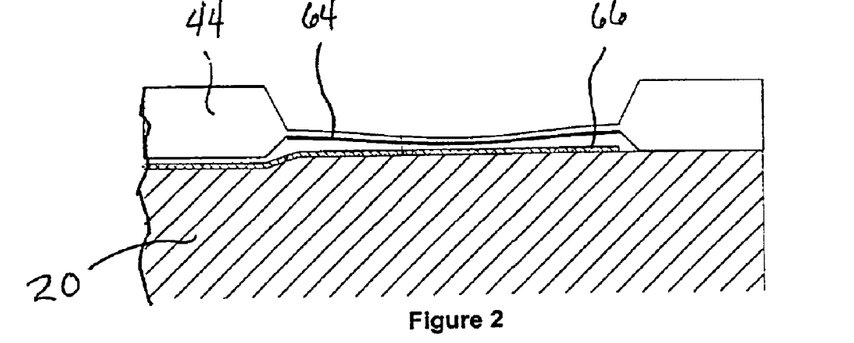
FIG. 2 is an enlarged cross-sectional view of the diaphragm portion of FIG. 1 operating in what is herein referred to as a "proximity" mode.

In the proximity mode of operation, generally seen in FIG. 2, the starting gap between the fixed electrode 66 and the moveable electrode 64, as well as the material and physical parameters for the diaphragm 64 itself, are chosen such that the fixed electrode 66 and the moveable electrode 64 will be spaced apart from one another over the entire operating pressure range of the sensor 18. For the standard equation of parallel plate capacitance, $C=\epsilon A/d$, the plate separation d will vary with the applied pressure, while the plate area A and the permittivity $\epsilon$ remain constant.

Figure 3:
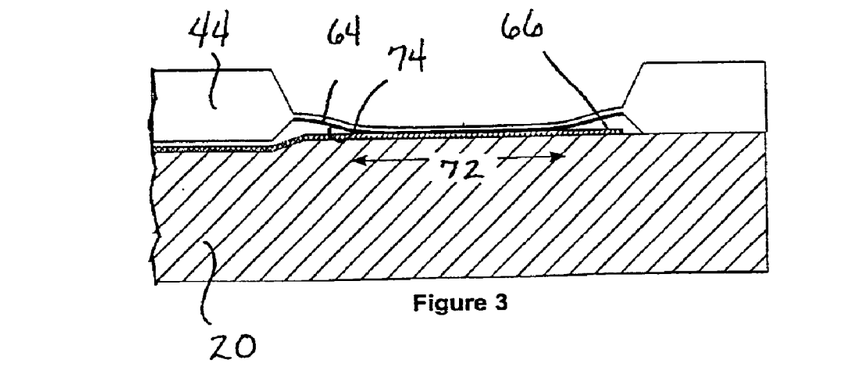
FIG. 3 is a cross-sectional view similar to that seen in FIG. 2 illustrating, however, the diaphragm operating in what is herein referred to as a "touch" mode.

In the touch mode of operation, generally seen in FIG. 3, the geometry (e.g., initial gap spacing between the fixed electrode 66 and the moveable electrode 64) as well as the material and physical parameters of the diaphragm 64 itself, are chosen such that the fixed electrode 66 and the moveable electrode 64 will progressively touch each other over the operating pressure range of the sensor 18. Accordingly, the area 72 of the fixed electrode 66 and the moveable electrode 64 in contact with each other will vary with the applied pressure. In the touch mode of operation, the dominant capacitance is the capacitance of the regions of the fixed electrode 66 and the moveable electrode 64 in contact with one another (if the dielectric coating 74 is thin compared to the total gap thickness, thereby yielding a relatively small effective plate separation distance d). Using the capacitance equation mentioned above, in the touch mode of operation, plate separation d and permittivity ϵ will remain substantially constant (at approximately that of the thickness of the dielectric layer 74), while the plate contact area A will vary with the applied pressure.

Figure 4:
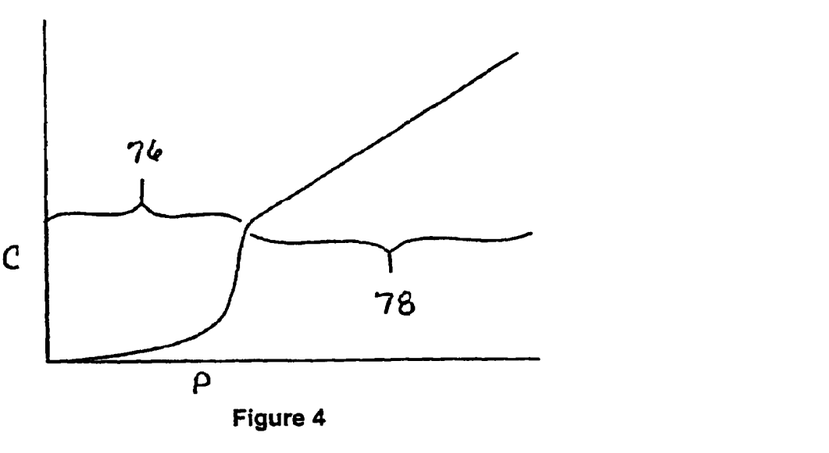
FIG. 4 is a capacitance versus pressure curve in the proximity and touch modes of operation.

In the graph of FIG. 4, capacitance-pressure relationship in the proximity and touch modes, respectively designated at 76 and 78, are seen. From a practical standpoint, the operational mode may be chosen based upon sensitivity, linearity, and dynamic range requirements. The touch mode typically yields higher sensitivity with a more linear output, but involves mechanical contact between surfaces and therefore requires a careful choice of the materials to avoid wear induced changes in performance of the pressure sensor 18.

Figure 5:
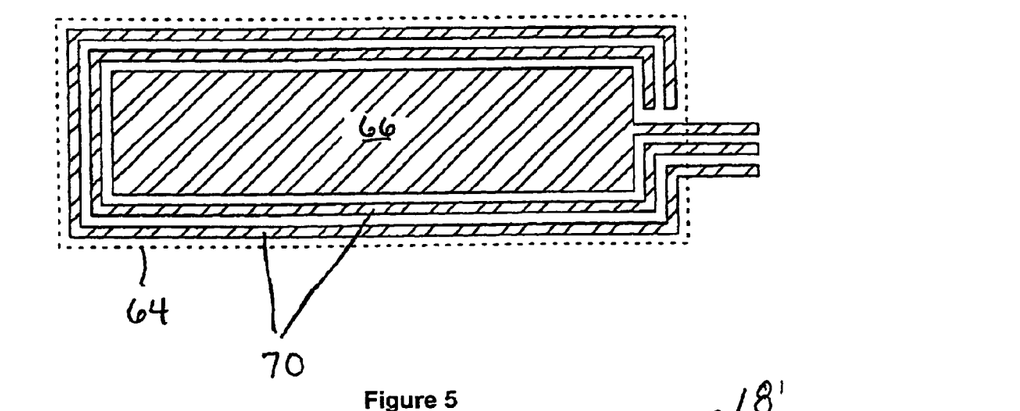
FIG. 5 is a top plane view of a second embodiment of the main electrode in the capacitive sensor portion of the implanted sensing device according to the principles of the present invention.

To improve performance of the capacitive pressure sensor 18 and as seen in FIG. 5, one or more secondary electrodes (designated at 70) may be located about the fixed electrode 66 near the projected edge of the diaphragm 64 where pressure induced deflection of the diaphragm 64 is minimal. The secondary electrodes 70 experience all of the capacitance-effecting phenomena seen by the main electrode 66, with the exception of any pressure-induced phenomena. The secondary electrodes 70, as such, operate as reference electrodes and by subtracting the secondary electrodes' capacitive measurement from the capacitive measurement of the main electrode 66, most or all non-pressure-induced capacitance changes (signal drift) may be filtered out. Examples as sources of signal drift, that may be filtered out by this method, include thermally induced physical changes and parasitics resulting from an environment with changing dielectric constant, such as insertion of the sensor into tissue.

Figure 6:
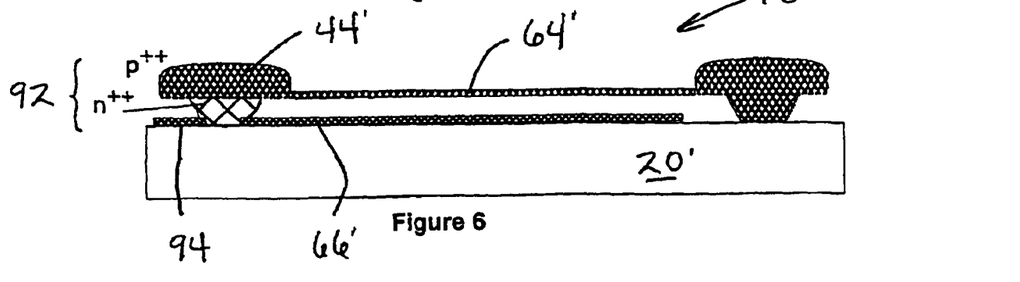
FIG. 6 is a diagrammatic illustration of one scheme for providing electrically isolated paths for the connections and electrodes of the capacitive sensor portion.

To isolate the internal volume 90 of the pressure sensor 18 and facilitate external electrical connection to the fixed and reference electrodes 66 and 70, a hermetic lead transfer is provided. The hermetic lead transfer may be accomplished by any of several means that provide a sealed and electrically isolated conductive path. One example, of a mechanism for achieving a sealed and electrically isolated conductive path is through the use of a p-n junction structure 92 in the sensor 18' of FIG. 6. The p-n junction structure 92 (with p-material forming the diaphragm) forms an electrically isolated path in a silicon layer and provides, in the illustrated construction, for electrical contact between a fixed electrode 66' on the substrate 20' and a lead trace 94, but not from the fixed electrode 66' to the diaphragm 64'.

Figure 7:
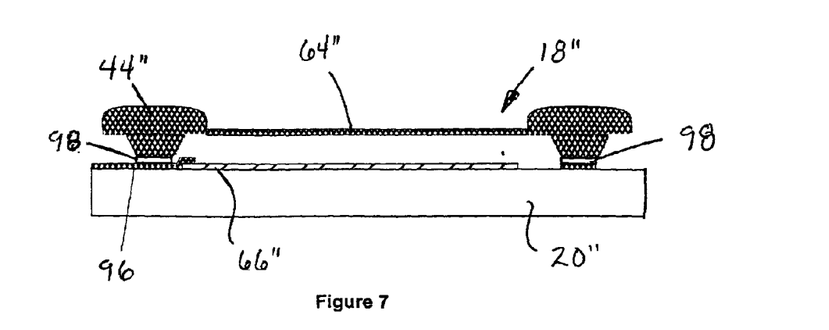
FIG. 7 is a diagrammatic illustration of another scheme for electrically isolating the conductive paths for the connections and contacts of the capacitive sensor portion.

In another alternative construction, seen in FIG. 7, a separate polysilicon layer 96 forms a conductive path to a fixed electrode 66". The conductive layer or trace 96 is insulated from the doped silicon cap layer 44" of the sensor 18" by a separate insulating layer 98.

Figure 8:
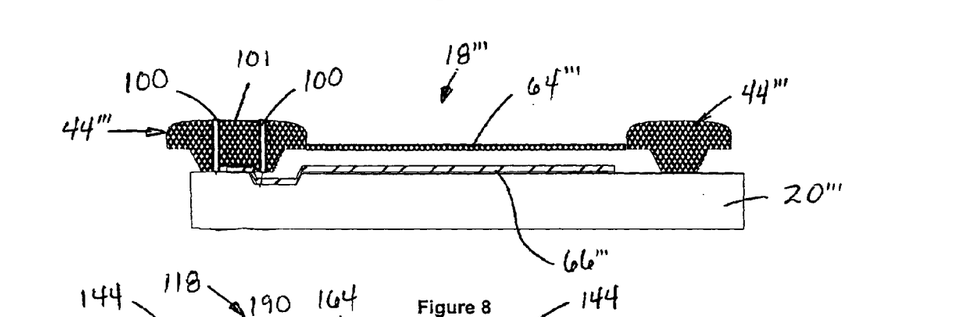
FIG. 8 is another diagrammatic illustration of a further scheme for electrically isolating the conductive paths for the connections and contacts of the capacitive sensor portion.

An additional alternative construction is presented in FIG. 8. Here, insulative barriers 100, formed of oxide, nitride or other non-conducting material, are used to isolate a conductive island 101 in the remainder of the doped silicon upper cap layer 44'''. The island 101 serves as a sealed conductive path for lead transfer to the fixed electrode 66''' of the sensor 18'''.

A key issue for sensing physiologic parameters in medical applications is that the sensor must be biocompatible. Biocompatibility involves two issues: the effect of the sensor on the body (toxicity), and the effect of the body on the sensor (corrosion rate). While the fabrication of the substrate 20 of Pyrex glass would be advantageous since Pyrex is highly corrosion resistant, additional measures must be taken to include the corrosion resistance for the silicon and other components of the sensor 18. One method of improving the silicon structures of the sensor 18, such as the upper cap layer 44, is to fabricate these structures of heavily boron-doped silicon. Heavily boron-doped silicon is believed to be largely corrosion resistant and/or harmless to tissues in biologic environments.

Another method, by which the corrosion resistance of the implanted sensor 18 may be improved, is through coating of the sensor 18 with titanium, iridium, Parylene (a biocompatible polymer), or various other common and/or proprietary thick and thin films. Such a coated device provides two levels of corrosion resistance: and underlying stable surface and a separate, stable coating (which may also be selectively bioactive or bioinert). Provided with these two levels of corrosion resistance, even if the outer coating contains pinholes, cracks, or other discontinuities, the sensor 18 retains a level of protection.

From an electrical standpoint, the capacitive sensor 18 of the present invention has advantages over other sensing methods, such as piezoresistive sensors. Specifically, the diaphragm 64 of the present sensor 18 may be kept at ground potential, which minimizes the possibility of galvanic corrosion (electrochemical etching of the silicon) and improved patient safety by eliminating the risk of stray currents. Furthermore, the capacitive sensor 18 of this invention has negligible power consumption. This makes the sensor 18 well suited to low-power applications, such as cardiac pacing, and other battery powered applications.

Most systems which require pressure as an input parameter typically prefer to receive the pressure measurement output in the form of a voltage, current, or frequency input instead of in the form of a capacitance. As such, it is generally useful to include signal conditioning or active circuitry with the sensor 18. Ideally, the conditioning circuitry should be placed as close to the sensor as possible to minimize parasitic capacitance due to the various leads between the sensor and the readout circuit.

Figure 9:
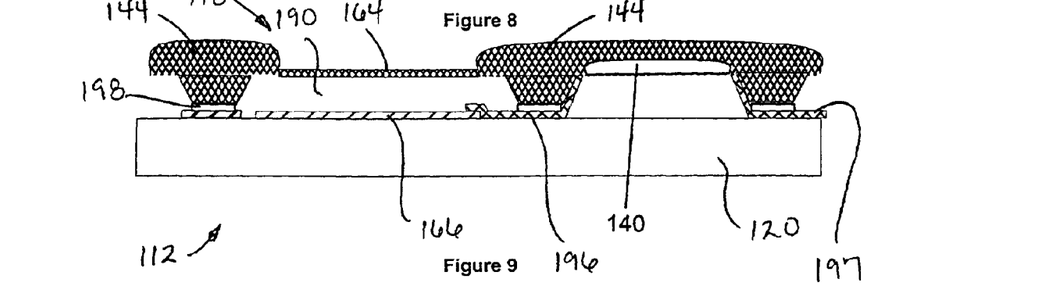
FIG. 9 is a cross-sectional view, generally similar to that seen in FIG. 1, further incorporating active circuitry into the sensing device.

An alternative embodiment of the present invention is an integrated capacitive sensor 118 of a sensing device 112 that includes active circuitry for immediate processing of the data including logging, error correction, encoding, analysis, multiplexing of multiple sensor inputs, etc. As seen in FIG. 9, the active circuitry can be integrated into the sensor 118 in many ways, including integrating active circuitry 140 into a silicon upper cap 144. In fabricating such a structure, the microfabrication process of the pressure sensor 118 is integrated with microfabrication of the circuitry 140. Many numerous designs and implementations of actual functions for the circuitry 140 are possible and well known to those familiar with the art. These designs and implementations are therefore not further discussed herein.

In FIG. 9, structures that are the same or similar to the structures seen in the previous embodiment are provided with corresponding 100 series designations and are not repetitively discussed. Reference is therefore directed to the preceding sections of this description where those corresponding structures are discussed.

As illustrated in FIG. 9, the fixed electrode 166 is electrically connected to conductive trace 196. Conductive trace 196 connects to circuitry 140 which in turn is connected to an output conductive trace 197 that leads to a readout device (not shown). To ensure electrical connection to the circuitry 140, traces 196 and 197 are insulated from the upper cap layer 144 by an appropriate and suitable insulator (not shown).

Figure 10:
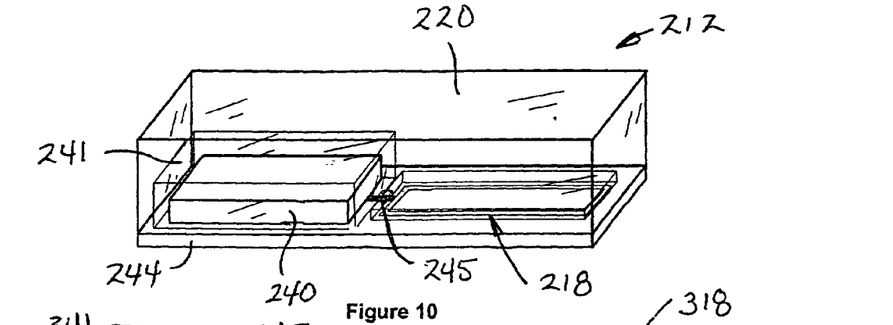
FIG. 10 is a schematic illustration illustrating another implementation of active circuitry into the microfabricated sensor.

Another approach to incorporating active circuitry 240 into a microfabricated sensing device 212 having an integrated capacitive pressure sensor 218 is illustrated in FIG. 10, which is an upside down view of the sensor 218. In this embodiment, the active circuitry 240 is attached to an interior surface of an upper cap layer 244. The circuitry 240 is accommodated within a recess 241 of the substrate 220 after microfabrication of the sensor 218. Electrical connections 245 may be integral with the substrate 220 or may later be added in.

Figure 11:
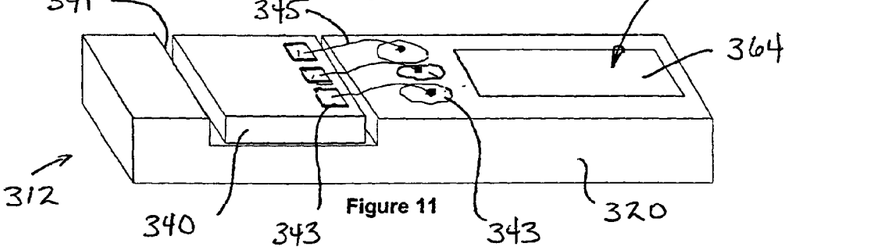
FIG. 11 illustrates another implementation of the of the circuitry into a recess in the substrate and with electrical connections being made by wire bonds.

In the embodiment seen in FIG. 11, a sensor 318 includes active circuitry 340 that is mounted within a recess 341 in a substrate 320. Notably, the circuitry 340 is not enclosed or sealed within a cap layer as in the prior embodiments. Suitable electrical connections are then made to bond conduction pads 342 on the circuitry 340 to corresponding pads 343 on the substrate 320. Preferably the pads 342 and 343 are located at the same height and wirebonds 345 are of a low profile to facilitate use of the microfabricated sensor 318 in restricted geometries.

As an alternative to the foregoing embodiments, the pressure sensor 18 of the sensing device 12 may be augmented and/or replaced with a structure or sensor 418 that allows a parameter other than pressure to be sensed. For clarity, in FIG. 12 only the sensor 418 portion of the sensing device 12 is shown, the non-illustrated elements being as previously discussed.

Figure 12:
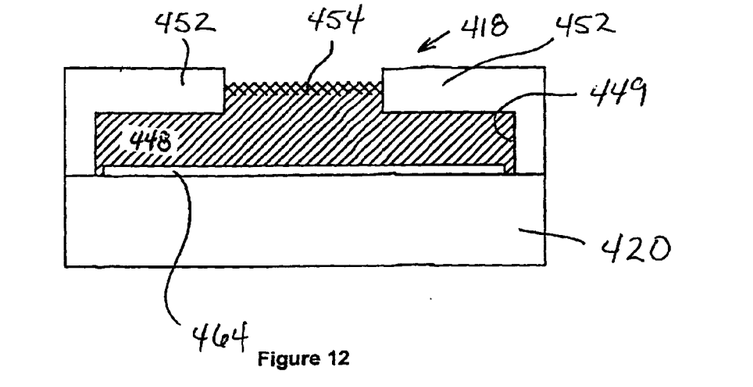
FIG. 12 illustrates a portion of a further embodiment of the present invention in which the pressure sensing features of the sensing device have been augmented over or replaced with a sensor allowing a parameter other than pressure to be sensed.

In the sensor 418, a chemical-sensitive substance 448 is placed in a confinement cavity 449 and in contact with an exterior surface of sensor diaphragm 464. Osmotic expansion of the substance 448, in response to the concentration of a target chemical, generates a pressure on the diaphragm 464 and allowing the concentration of the chemical to be monitored. For convenience, only the substrate 420 is illustrated, the fixed electrode and associated structures be omitted. This sensor 418 may optionally include cap structure 452 to restrict the expansion of the chemical sensitive substance 448 to the center of the diaphragm 464 to maximize deflection of the diaphragm 464. A micro-machined mesh, grid, or semi-permeable membrane 454, also optional and either integral to the cap or attached separately thereto, may be included to prevent the chemical sensitive substance 448 from escaping (or bulging out of) the confinement cavity 449, and/or to prevent foreign materials from entering the cavity 449. The mesh 454 could also exist on the molecular level, being formed of a material such as a cross-linked polymer.

In another alternative parameter sensing embodiment, a material with high thermal coefficient of expansion is placed between moveable and fixed electrodes in a structure otherwise constructed similar to a capacitive sensor structure, thereby forming a temperature sensor.

Figure 13A:
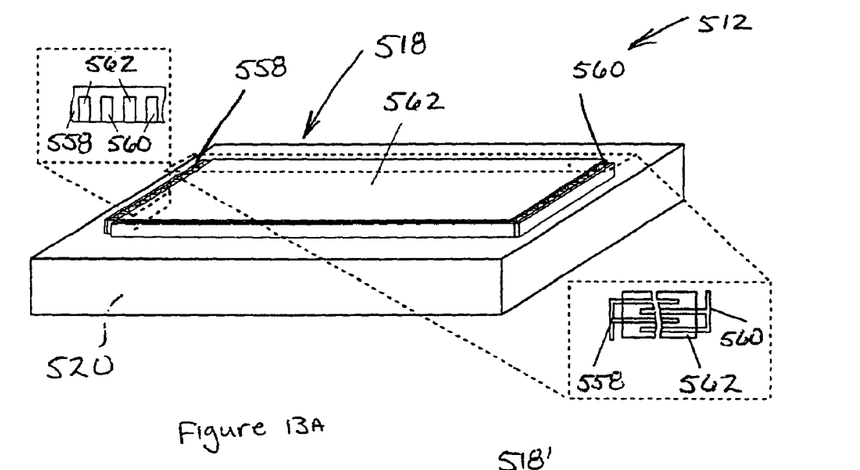
FIG. 13A is schematic perspective view, with portions enlarged, illustrating an alternative embodiment for sensing according to the principles of the present invention.
Figure 13B:
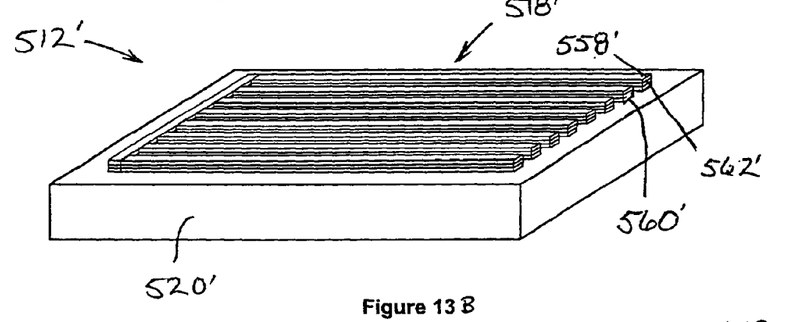
FIG. 13B is an embodiment generally similar to that seen in FIG. 13A for sensing according to the principles of the present invention.

FIG. 13A illustrates a sensing device 512 having an alternative capacitive pressure sensor 518 on a substrate 520, additional structures are omitted for clarity. In this sensor 518, the capacitance changes due to a varying dielectric constant within the capacitive gap defined between electrodes 558 and 560. The gap is filled with sensing substance 562 chosen such that its dielectric constant changes in response to the particular physiologic stimulus being evaluated. FIG. 13B depicts an alternate implementation of the above embodiment, with the electrodes 558' and 560' and the sensing substance 562' being stacked vertically on the substrate 520, as opposed to the lateral orientation in FIG. 13A.

Figure 14:
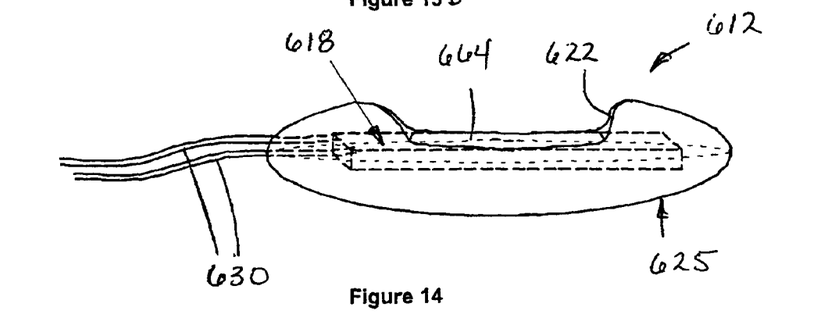
FIG. 14 illustrates a sensing device, according to the principles of the present invention, encapsulated in a material yielding a pellet-like profile for implantation into the tissues in the body of a patient.

In FIG. 14, the sensing device 612 is encapsulated in a biocompatible material such as poly(methyl methacrylate) (PMMA), yielding a pellet-like profile designated as 625. A recess 622 is formed in the pellet 625 allows intimate access to the movable element 664 or sensing surface. In addition to providing an alternate form factor that may be less mechanically irritating to tissue, both during and after implantation, such an embodiment may better allow the sensing device 612 to be incorporated into the body of a medical device, such as an extrusion, injection-molded part, soft rubber, or other material, that otherwise would poorly anchor to a rectangular or other geometrically shaped sensing device 12. Leads 630 are provided so as to extend from the profile 625 enabling it to be coupled to other devices. Provided in this manner, strain on the leads 625 is reduced. Obviously, encapsulation could be used to give the sensing device other profiles or form factors as well.

Figure 15:
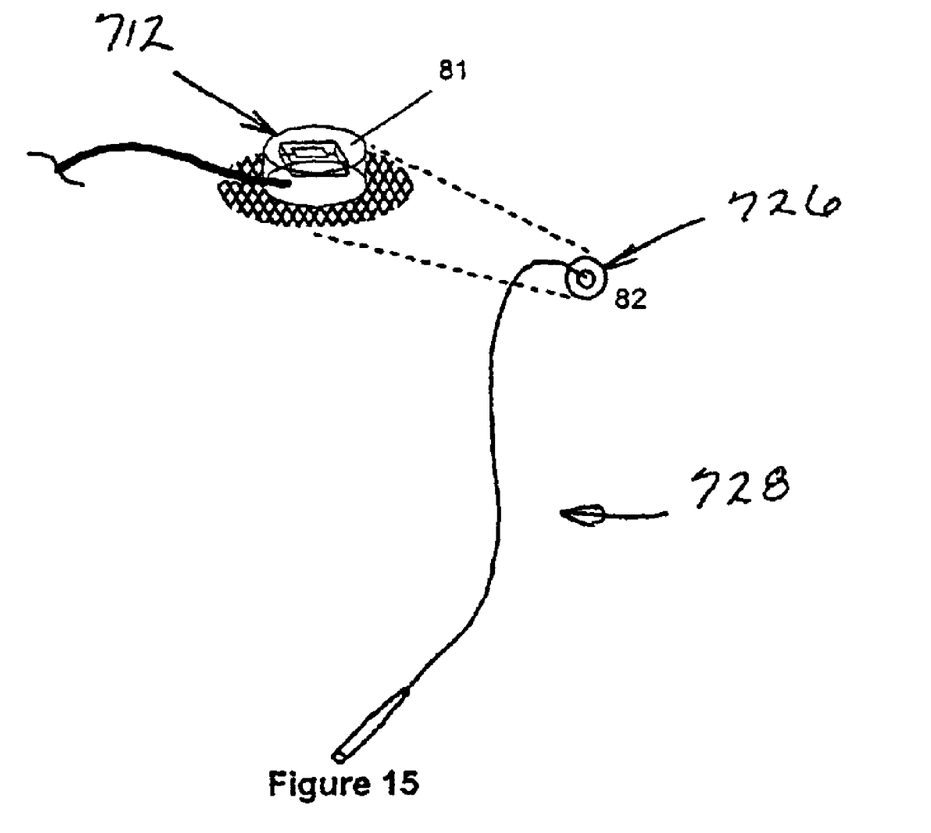
FIG. 15 illustrates a sensing device according to the principles of the present invention being located within the electrode tip of an implantable stimulation lead, such as that used for cardiac pacing.

One application of the described technology, depicted in FIG. 15, locates the microfabricated sensing device 712 in an electrode tip 726 of an implantable stimulation lead 728, such as a stimulation lead used for cardiac pacing. In such an arrangement, the sensing device 712 could be used with a read-out device (not shown) for monitoring arterial, atrial, ventricular, and/or other blood pressures. The low power requirements of the device 712 are ideal for battery powered implantable devices such as pacemakers and defibrillators. The interface circuit facilitates a low impedance signal path in the lead, which is critical for such applications. Typically, the silicone rubber encapsulant used for pacing leads absorbs mobile ions from the surrounding tissue over time. This reduces the bulk resistivity of the silicone rubber to the order of ten kilograms, a high-impedance signal path would see a short across the internal pacing lead wires.

A number of different, and at times application-specific, schemes can be envisioned for long-term use of the sensing device 12 of the present invention. In general, it is necessary to anchor the device 12 so that migration of the device 12 does not occur within the patient. A dislodged device 12 may migrate away from the physiologic parameter intended to be sensed, thereby rendering the device 12 useless for its intended purpose and requiring implantation of another device 12. A variety of such anchoring schemes is discussed below.

To secure the device in position for monitoring of the desired parameter, a screw (or stud) may be attached to the lower surface of the sensing device. Preferably, the screw is attached to the lower surface with biocompatible epoxy or a similar method. The screw is then embedded into tissue of the patient and the device retained in place. Preferred materials for the screw include stainless steel or titanium.

From the above, it can be seen that many applications exist for the system 10 of the present invention. Some illustrative examples of such applications are described hereafter.

The pressure, temperature or other data sensing technology, in its various forms, may be incorporated into an open or closed-loop therapeutic system for the treatment of medical conditions which require or benefit from regular, subcutaneous monitoring of pressures or other parameters. The system may be used, for example, to control the administration of drugs. One particular application of this would be to control hyper- or hypotension. In the preferred embodiment, pressure data from the sensor, alone or in conjunction with other real-time or preexisting data, is used to adjust drug or other therapy for hypo- or hypertensive patient. Therapy is provided by means of a control module worn by, or implanted within, the patient (similar to e.g., an insulin pump for diabetics). The module may alert the user to take action, directly administer a drug intravenously, and/or initiate other invasive or non-invasive responses. Furthermore, relevant information (including, but not limited to, measure physiologic parameters, treatment regimens, data histories, drug reservoir levels) can further be transmitted from the control module to other locations via cellular phone, wireless infrared communication protocols or other communication methods and mechanisms.

Other applications of the implantable wireless sensing device of this invention include, without limitation, the following: a) Monitoring congestive heart failure patients such as left ventricle pressure monitoring, left atrium pressure monitoring and pulmonary artery pressure monitoring; 2) other hemodynamics parameters including blood pressure, blood flow velocity, blood flow volume and blood temperature; 3) diabetic applications including glucose level monitoring; 4) urinary applications such as bladder pressure and urinary tract pressure measuring; and 5) other blood parameters including $O_2$ saturation, pH, $CO_2$ saturation, temperature, bicarbonate, glucose, creatine, hematocirt, potassium, sodium, chloride; and 6) cardiac parameters including (previously discussed) valve pressure gradients and stent pressure gradients.

In addition to single sensor, an array of different sensors may be fabricated or assembled on one sensing device to enhance artifact removal and/or selectivity/differentiation between signals. A discussion of such a construction best details this construction. Local pressure or pH variations can add spurious signals to a pressure- or pH-based glucose sensor. To compensate for these spurious signals, adjacent pH or pressure reference sensors may be implemented to measure these environmental parameters. External sensors may also be used to compensate for factors such as atmospheric pressure. A combination of sensor arrays, fuzzy logic, look-up tables, and/or other signal-processing technologies could all be used to effect such compensation.

The foregoing disclosure is the best mode devised by the inventor for practicing the invention. It is apparent, however, that several variations in accordance with the present invention may be conceivable to one of ordinary skill in the relevant art. Inasmuch as the foregoing disclosure is intended to enable such person to practice the instant invention, it should not be construed to be limited thereby, but should be construed to include such aforementioned variations, and should be limited only by the spirit and scope of the following claims.

What is claimed is:

1. An implantable microfabricated sensing device capable of being entirely implanted within a human body for measuring a physiologic parameter of said human body, said sensing device comprising a biocompatible monolithic structure comprising:
   a substrate;
   a sensor integrally microfabricated with said substrate and being responsive to the physiologic parameter;
   at least one conductive path integrally formed with said substrate and said sensor; and
   active circuitry microfabricated in proximity to said sensor and electrically connected to said sensor by said conductive path.

2. The sensing device of claim 1 wherein said sensor is a capacitive sensor having a fixed electrode and a moveable electrode.

3. The sensing device of claim 1 wherein said sensor comprises a cap layer on said substrate.

4. The sensing device of claim 3 wherein said cap layer includes positions defining a diaphragm of said sensor.

5. The sensing device of claim 3 wherein said active circuitry is integrally fabricated in said substrate.

6. The sensing device of claim 3 wherein said cap layer is formed of monocrystalline silicon.

7. The sensing device of claim 3 wherein said cap layer is boron doped silicon.

8. The sensing device of claim 2 wherein said fixed and moveable electrodes define an interior volume therebetween and a surface activity in said substrate defines a displacement cavity in communication with said interior volume.

9. The sensing device of claim 2 wherein said fixed electrode includes a main electrode and at least one reference electrode.

10. The sensing device of claim 1 wherein said sensing device is entirely implanted within said human body and is operating to measure the physiologic parameter within said human body.

11. The sensing device of claim 1 further comprising a cap layer formed over said substrate.

12. The sensing device of claim 11 wherein said cap layer includes a portion defining a moveable electrode of said sensor.

13. The sensing device of claim 11 wherein said cap layer is conductive.

14. The sensing device of claim 12 wherein said cap layer is doped silicon.

15. The sensing device of claim 1 wherein said sensor is a pressure sensor.

16. The sensing device of claim 1 wherein said sensor is a temperature sensor.

17. The sensing device of claim 1 wherein said sensor is a chemical sensor.

18. The sensing device of claim 1 further comprising a cap layer bonded to said substrate, said active circuitry being integrally formed in said cap layer.

19. The sensing device of claim 1 wherein said active circuitry is integrally formed in said substrate.

20. The sensing device of claim 1 wherein said active circuitry is mounted to said substrate.

21. The sensing device of claim 20 wherein said active circuitry is received within a recess defined in said substrate.

22. The sensing device of claim 1 further comprising at least two sensors.

23. The sensing device of claim 22 wherein said two sensors sense the same physiologic parameter.

24. The sensing device of claim 22 wherein said two sensors sense different physiologic parameters.

25. The sensing device of claim 1 wherein said sensor is a capacitive sensor having a fixed electrode and a moveable electrode, said fixed and moveable electrodes being electrically coupled by first and second conductive paths to said active circuitry, said first and second paths being electrically isolated from one another.

26. The sensing device of claim 25 wherein said paths are isolated by a dielectric layer therebetween.

27. The sensing device of claim 25 wherein said paths are isolated by a p-n junction structure.

28. The sensing device of claim 25 wherein said sensor operates in a proximity mode whereby the fixed electrode and the moveable electrode do not contact each other when responding to the physiologic parameter.

29. The sensing device of claim 25 wherein said sensor operates in a touch mode whereby the fixed electrode and the moveable electrode progressively contact each other when responding to the physiologic parameter.

30. The sensing device of claim 1 further comprising a bioinert coating over a majority of exterior surfaces of said sensor.

31. The sensing device of claim 1 further comprising a housing defining a form factor providing an external shape to said sensing device that differs from the monolithic structure.

32. The sensing device of claim 31 wherein said housing is of a non-rigid material.

33. The sensing device of claim 31 wherein said housing is a plastic material.

34. The sensing device of claim 31 wherein said housing comprises a recess providing intimate access to the sensor.

35. The sensing device of claim 2 wherein said fixed electrode is a conductive layer on said substrate.

* * * * *